(12) United States Patent
Sutherland et al.

(10) Patent No.: US 10,173,020 B2
(45) Date of Patent: Jan. 8, 2019

(54) DEVICES AND METHODS FOR IDENTIFICATION OF MEDICAMENT DELIVERY DEVICES

(71) Applicant: ADHERIUM (NZ) LIMITED, Auckland (NZ)

(72) Inventors: Garth Campbell Sutherland, Auckland (NZ); Michael James Gormack, Auckland (NZ); Kin Lung Chan, Lower Hutt (NZ); Terry Palmer, Lower Hutt (NZ)

(73) Assignee: ADHERIUM (NZ) LIMITED, Auckland (NZ)

( * ) Notice: Subject to any disclaimer, the term of this patent is extended or adjusted under 35 U.S.C. 154(b) by 0 days.

(21) Appl. No.: 15/311,472

(22) PCT Filed: May 15, 2015

(86) PCT No.: PCT/NZ2015/000037
§ 371 (c)(1),
(2) Date: Nov. 15, 2016

(87) PCT Pub. No.: WO2015/174856
PCT Pub. Date: Nov. 19, 2015

(65) Prior Publication Data
US 2017/0173279 A1 Jun. 22, 2017

(30) Foreign Application Priority Data

May 16, 2014 (NZ) .......................................... 625105
Dec. 5, 2014 (NZ) .......................................... 702707

(51) Int. Cl.
*G01N 21/00* (2006.01)
*A61M 15/00* (2006.01)
*G01N 21/3563* (2014.01)

(52) U.S. Cl.
CPC ...... *A61M 15/008* (2014.02); *A61M 15/0021* (2014.02); *G01N 21/3563* (2013.01);
(Continued)

(58) Field of Classification Search
CPC ................ A61M 15/00; A61M 15/008; A61M 15/0021; A61M 15/0065; A61M 15/009;
(Continued)

(56) References Cited

U.S. PATENT DOCUMENTS

| 2003/0098022 A1 | 5/2003 | Nakao et al. | |
| 2012/0240923 A1* | 9/2012 | Denyer | A61M 15/00 128/202.22 |
| 2014/0000598 A1* | 1/2014 | Sutherland | A61M 15/0065 128/203.12 |

FOREIGN PATENT DOCUMENTS

| WO | 2002005879 A1 | 1/2002 |
| WO | 2003092773 A1 | 11/2003 |

(Continued)

OTHER PUBLICATIONS

International Search Report issued in PCT/NZ2015/000037 dated Sep. 10, 2015.
Written Opinion issued in PCT/NZ2015/000037 dated Sep. 10, 2015.

*Primary Examiner* — Jamil Ahmed
(74) *Attorney, Agent, or Firm* — Kenealy Vaidya LLP

(57) ABSTRACT

Some embodiments are directed to a compliance monitor for monitoring usage of a medicament delivery device that includes a store of medicament, and a medicament dispenser for delivering a dose of medicament. The compliance monitor includes a compliance monitor housing configured to attach to the medicament delivery device, a dose detector for determining when a dose of medicament is dispensed, and a recognition module for identifying the properties of the medicament delivery device.

33 Claims, 10 Drawing Sheets

Figure 1:
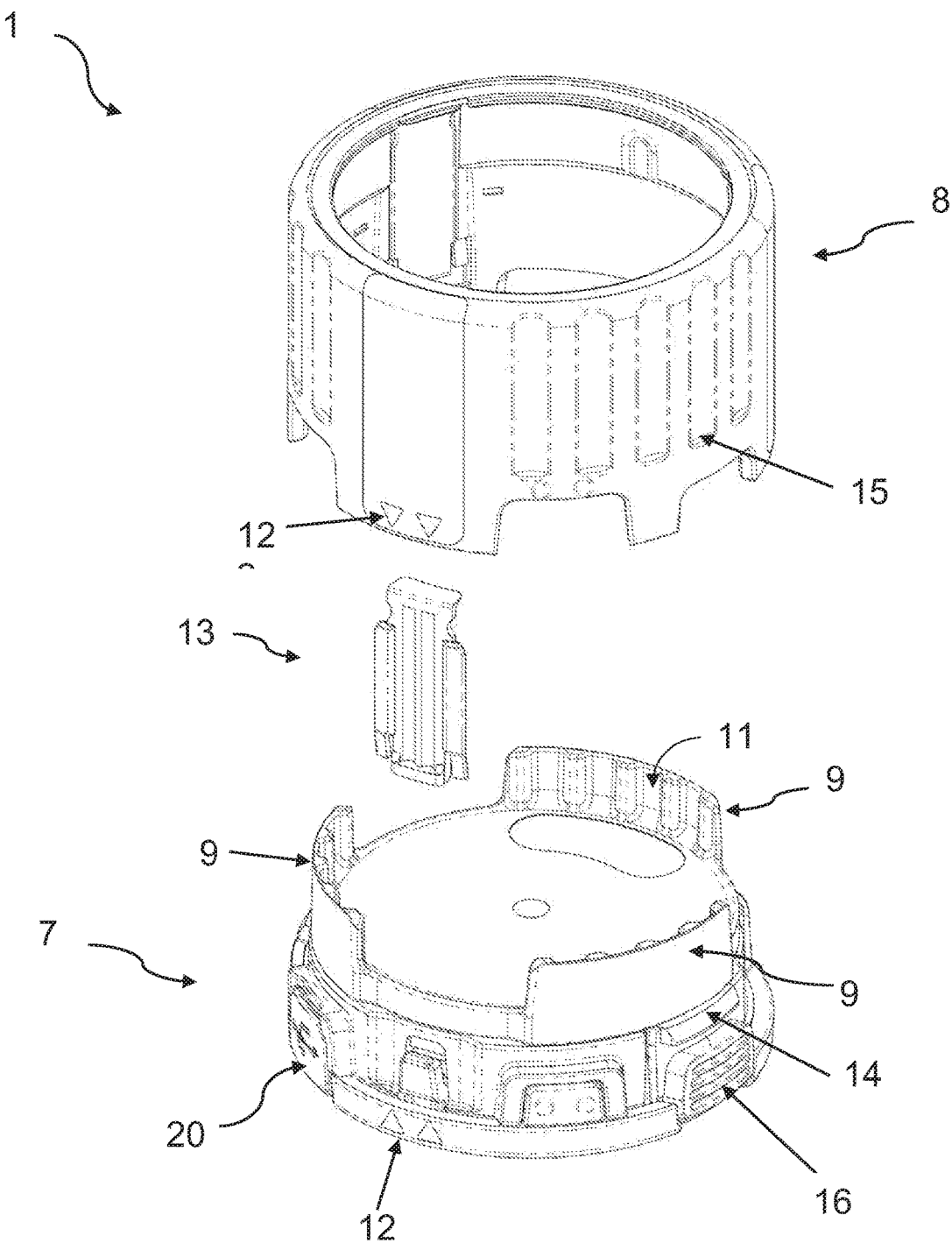

(52) U.S. Cl.
CPC ....... *A61M 15/009* (2013.01); *A61M 15/0065* (2013.01); *A61M 2202/06* (2013.01); *A61M 2205/14* (2013.01); *A61M 2205/18* (2013.01); *A61M 2205/332* (2013.01); *A61M 2205/3306* (2013.01); *A61M 2205/3313* (2013.01); *A61M 2205/3317* (2013.01); *A61M 2205/3331* (2013.01); *A61M 2205/3368* (2013.01); *A61M 2205/3375* (2013.01); *A61M 2205/3592* (2013.01); *A61M 2205/502* (2013.01); *A61M 2205/505* (2013.01); *A61M 2205/52* (2013.01); *A61M 2205/6018* (2013.01); *A61M 2205/6081* (2013.01)

(58) Field of Classification Search
CPC .......... A61M 2202/06; A61M 2205/14; A61M 2205/18; A61M 2205/3306; A61M 2205/3313; A61M 2205/3317; A61M 2205/332; A61M 2205/3331; A61M 2205/3368; A61M 2205/3592; A61M 2205/502; A61M 2205/505; A61M 2205/52; A61M 2205/6018; A61M 2205/6081; G01N 21/3563; G01J 3/51; G01J 3/50

See application file for complete search history.

(56) References Cited

FOREIGN PATENT DOCUMENTS

| WO | 2004011070 A1 | 2/2004 |
| WO | 2010114392 A1 | 10/2010 |
| WO | 2011073806 A1 | 6/2011 |
| WO | 2011083377 A1 | 7/2011 |

* cited by examiner

FIG 1 *(PRIOR ART)*

FIG 2 *(PRIOR ART)*

DEVICES AND METHODS FOR IDENTIFICATION OF MEDICAMENT DELIVERY DEVICES

CROSS REFERENCE TO RELATED APPLICATION(S)

This application is a National Phase filing under 35 C.F.R. § 371 of and claims priority to PCT Patent Application No.: PCT/NZ2015/000037, filed on May 15, 2015, which claims the priority benefit under 35 U.S.C. § 119 of New Zealand Application Nos.: 625105 and 702707, filed on May 16, 2014 and Dec. 5, 2014, respectively, the contents of each of which are hereby incorporated in their entireties by reference.

FIELD

This invention relates to devices and methods for identification of medicament delivery devices.

The invention may be particularly suitable for use with medicament delivery devices such as pressurised metered dose inhalers and dry powder inhalers, and/or compliance monitors associated with same.

However, it is to be understood and appreciated that the invention is not to be limited to such use. For example, the invention may also be suitable for use with other medicament delivery devices (and/or compliance monitors associated with same), for example infusion systems, injection devices, nebulisers, oral medicament dispensers, transdermal devices and respiratory therapies.

The prior art and possible applications of the invention, as discussed below, are therefore given by way of example only.

BACKGROUND

The use of medicament inhalers for the treatment of respiratory diseases is well known. A common type of medicament inhaler is what is known as a pressurised Metered Dose Inhaler (pMDI). The construction and operation of pMDIs is well known and described in prior art.

Another common type of medicament inhaler is what is known as a Dry Powder Inhaler (DPI). The construction and operation of DPI's is also well known and described in prior art.

Further examples of medicament inhalers include delivery devices such as nebulisers and nasal sprays. Such delivery devices are generally designed to supply a dose of medicament in the form of a fine mist, which is directed either into the month or nasal cavity of a user.

A problem or difficulty associated with the use of medicament inhalers generally is poor medicament compliance, particularly in relation to the use of preventer medicament inhalers. That is, many studies have shown that users frequently do not take their medicament at the predetermined or prescribed times and/or in the required amounts.

The consequences of this non-compliance are reduced disease control, lower quality of life, lost productivity, hospitalisation and avoidable deaths.

Not only is compliance to preventative medicaments typically low, but it has also been shown that actual compliance by a user is lower than the same user's estimated compliance.

In order to address the issue of poor medicament compliance, there are available a number of compliance monitoring devices for use with medicament inhalers. Examples include those described in U.S. Pat. No. 6,958,691 Anderson; U.S. Pat. No. 8,342,172 Levy; U.S. Pat. No. 6,202,642 McKinnon; U.S. Pat. No. 5,544,647 Jewett; U.S. Pat. No. 8,464,707 Jongejan; US2014/0000598 Sutherland; U.S. Pat. No. 8,424,517 Sutherland; WO 2013/043063 Sutherland; and NZ622000 Sutherland.

Some of these prior art devices include a detection means to determine when a canister of medicament has been inserted into and/or removed from an actuator of a pMDI. Examples include US2014/0000598 Sutherland and WO 2013/043063 Sutherland.

Furthermore, US2014/0000598 Sutherland discloses a detection means for determining if a pMDI actuator (containing a canister of medicament) has been placed into and/or removed from a releasably attachable compliance monitor housing. Likewise, NZ622000 Sutherland discloses a detection means for determining when a compliance monitor has been attached to and/or removed from a DPI. US2014/0000598 Sutherland also discloses an optical dose counter which may be adapted to determine any deterioration of the inner surfaces of the medicament inhaler.

However, none of the above three compliance monitors are capable of identifying the medicament delivery device they are attached to.

Medicaments used to control asthma are broadly grouped into three classes: relievers, preventers, and long acting relievers. In addition, there are also available combination medicaments which combine both a reliever and a preventer medicament. These classifications can also be applied to the inhalers themselves (both pMDI's and DPI's).

A reliever (or rescue) medicament (or inhaler) is used in a specific event or emergency, for example, if a person were to have a sudden asthma attack. A reliever medicament generally contains a bronchodilator used to open up the airways (e.g., Bricanyl® TURBUHALER® by AstraZeneca). The relievers are fast acting and in most cases will relieve (or reduce the severity of) an asthma attack, almost instantaneously.

Preventer (or controller) medicaments are designed for regular use in order to prevent an asthma attack from occurring and/or to manage or control asthma. They treat the underlying inflammation in the airways and generally contain corticosteroids (e.g., Pulmicort® TURBUHALER® by AstraZeneca). The regular use of a preventer by asthma sufferers is generally effective in controlling the disease and/or preventing the vast majority of asthma attacks. Commonly, preventers are taken twice a day, usually at a set time in the morning and in the evening. Importantly, a preventer will not relieve an acute asthma attack that has already started.

Long acting reliever medicaments (or long acting rescue medicaments) generally contain long acting bronchodilators (e.g., Oxis® TURBUHALER® by AstraZeneca). Long acting reliever medicaments should be taken regularly and are often taken together with preventers.

Symbicort® TURBUHALER® by AstraZeneca is an example of a combination medicament.

To assist patients with treatment regime compliance and/or to enable them to distinguish between their different medicaments, pharmaceutical companies generally colour-code their medicaments and/or inhalers.

For example, a blue colour is often used for reliever medicaments (e.g. Bricanyl® TURBUHALER®, Ventolin® pMDI); an orange or brown colour is often used for preventer medicaments (e.g. Plumicort® TURBUHALER®, Flixotide® pMDI); long acting relievers, such as Oxis® TURBUHALER® are often green/blue; a red colour is often used for the actuator (base) of the combined preventer and reliever (e.g., Symbicort® TURBUHALER®) and purple for pMDI combination inhaler (Seretide®).

Patients suffering from respiratory conditions are usually prescribed at least two of these types of medicaments in order to properly manage and/or treat their condition (typically a reliever medicament and a preventer medicament).

Notwithstanding the differences in outer appearance (colour) of the inhalers, patients nonetheless often use the wrong medicament for the intended purpose. For example, they use a reliever where a preventer should be used or vice versa, or use a reliever when a long acting reliever should be used.

It will be appreciated that problems may occur if the patient inadvertently uses the wrong medicament, for example, if they use a reliever medicament where a preventer medicament should have been used or vice versa; or if they were to use a reliever medicament when a long acting reliever should have been used, and so on.

Having regard to the forgoing, it may be of advantage if there was available a compliance monitoring device capable of distinguishing between the different types of medicaments and/or inhalers—with a view to possibly alerting the patient (or a healthcare professional) if the wrong medicament or inhaler has been (or is about to be) used.

In U.S. Pat. No. 7,191,777 Brand and U.S. Pat. No. 7,819,116 Brand there is described a medicament dispenser system which uses radio frequency identification to identify the medicament used in conjunction with the actuator. A key disadvantage of both Brand patents is that the identification method requires modification of the medicament delivery device through: (a) the addition of a RFID tag to the medicament canister and (b) the addition of a RFID reader to the actuator. Furthermore, the solution proposed by both Brand patents is complex and not cost effective.

Optical proximity sensors, colour sensors and sensors combining both are well known in the art.

Optical proximity sensors such as those described in U.S. Pat. No. 8,232,883 Yao comprise an integrated infrared emitter or light source and a corresponding photodiode or light detector embedded into a housing and connected to a light detector sensing circuit. U.S. Pat. No. 8,232,883 Yao describes an optical sensor comprising infrared light (IR) emitter (E) and IR detector (D) mounted on a substrate. The axis of the IR E and IR D are parallel and vertical. Two spherical lenses are placed over the IR E and IR D to collect and direct the light either onto the object to be detected (lens over IR E) or to the IR D (lens over IR D). The sensor also comprises a light shield dividing the sensor into a light emitting and light detection portions, to minimize the crosstalk, increase the detection distance, reducing the size, volume and footprint of the sensor and manufacturing costs.

We have previously described compliance monitoring devices which use optical sensors for dose detection in our NZ Patent No. NZ 574666 Sutherland. The optical sensor could be adapted to monitor and/or store data relating to when a medicament container has been removed from and/or placed into the actuator. However, the devices of our earlier invention did not have the function of identifying the type of medicament delivery device being monitored.

Photoelectric colour sensors generally comprise three light emitters, each generating wavelength bands corresponding to red (R), green (G) and blue (B) respectively, a lens for emitting the light from each emitter to the object to be detected and a light receiver. The R, G, B light is emitted at the object in a pre-set order. The colour of the object is determined by reference to the ratios between the red, green, and blue wavelengths reflected by the object as detected by the receiver. U.S. Pat. No. 6,323,481 Ueki describes a fibre-type photoelectric switch which is capable of detecting presence, absence, the shape, dimensions and colour of an object on the basis of the reception of reflected light.

Chip colour sensors generally contain an array of red, blue and green filter photodiodes in various arrangements. The light signal from the photodiodes is converted to a frequency (light-to-frequency converter, e.g. TCS3772) or to a digital signal (light-to-digital converter, e.g., TAOS TCS230) and then the conversion result is transferred to the corresponding data registers in the microcontroller for processing. The digital signal intensities are compared to determine the predominant colour in the guided light and hence the predominant colour of the object.

Compliance monitoring devices are relatively small, portable and light. Any sensor incorporated into a compliance monitor has to be small, light-weight, have low-power use and low manufacturing cost and be capable of detection at very short distances, with a preferred range being between 0.1-5 mm, even in cases of non-reflective surfaces.

There are available optical detection systems whereby a light emitter is placed next to a light receiver, and whereby the axis of the light emitter (or light emitted) is parallel to the axis of the light receiver (that is, both axes are usually vertical). In such a system, the light receiver is able to receive and/or detect light emitted by the light emitter, after it has been reflected off the surface of an adjacent object, thereby identifying that the object is present. However a disadvantage, or limitation, of such a system is that it only works for object surfaces that are reflective. If the surface of the object is non-reflective and/or absorbent, then most of the light emitted will be absorbed rather than reflected, and hence no significant amount of reflected light will be received and/or detected by the light receiver. In such instances the light receiver may erroneously conclude that no object is present.

There are also available optical detection systems in which the axis of the light emitter is angled towards the axis of the light receiver (e.g. Omron EE-SY190/191), but their detection range renders them not suitable for use in compliance monitors.

While optical colour sensor chips (e.g., TAOS TCS3772 colour light-to-digital converter with proximity sensor) generally fit the size and detection distance criteria, there are some disadvantages associated with their use in compliance monitors:

Cost—colour sensor chips are relatively expensive and furthermore they require additional parts such as external visible and infrared LED illumination sources.

Power usage—the sensor chips contain internal processing and have significantly higher times for initialisation and signal acquisition leading to higher power consumption.

Sensitive to ambient light—the sensor chips are prone to saturation due to the use of the visible light range and relative intensity of the illumination source.

WO2014/023763 Schabbach describes a supplemental device for a pen-type injection device, which includes a quantity determiner for determining a quantity of medicament that has been dispensed. In one embodiment, the quantity determiner comprises a light source and a photo sensor, operatively connected to a processor arrangement which is configured to interpret signals provided by the photo sensor to determine the quantity of medicament that has been delivered.

WO2013/109913 Bear describes a medication storage device which includes an imaging system, comprising a plurality of image capturing devices, to capture images of the medication dose containers. However, the invention described in Bear only discloses the use of a camera—type device to capture these images, and furthermore, the image capturing devices described in Bear are only adapted to capture images of the interior region of each dose container.

WO2011/073806 Denyer describes a monitoring device which includes a housing adapted to be releasably attached to a drug delivery device. The housing includes a colour detector adapted to detect and/or identify a colour associated with the drug delivery device. The colour detector described in Denyer comprises a plurality of light sources adapted to produce different coloured light, and a colour-sensitive photodetector for determining the colour of the drug delivery device, based on the reflected coloured light. Hence, one limitation associated with Denyer is that it is only able to utilise visible (or coloured) light sources.

OBJECT

It is an object of the present invention to provide a compliance monitor for monitoring usage of a medicament delivery device which goes some way towards addressing some of the aforementioned problems or difficulties, or which, at the very least, provide the public with a useful choice.

It is a further object of the present invention to provide an optical sensor, for use with a compliance monitor, which goes some way towards addressing some of the aforementioned problems or difficulties, or which, at the very least, provide the public with a useful choice.

DEFINITIONS

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

STATEMENTS OF INVENTION

According to one aspect of the present invention, there is provided a compliance monitor for monitoring usage of a medicament delivery device, the medicament delivery device including:
a) a store of medicament;
b) a medicament dispensing means for delivering a dose of medicament,
and the compliance monitor including:
c) a compliance monitor housing adapted to attach to the medicament delivery device,
d) a dose detection means for determining when a dose of medicament is dispensed,
e) a recognition means for identifying the properties of the medicament delivery device.

Preferably, the medicament delivery device may be a metered medicament inhaler, for example a pMDI or a DPI used for the treatment of respiratory diseases such as asthma, COPD, cystic fibrosis, bronchiectasis, and so on. However, it is to be understood and appreciated that the compliance monitor may also be used with other medicament delivery devices, for example infusion systems, injection devices, nebulisers, oral medicament dispensers, transdermal devices, pill boxes and respiratory therapies.

The compliance monitor housing may be of any suitable size, shape or configuration as required or desired, or as dictated by the type or configuration of the medicament delivery device.

In one embodiment, the compliance monitor housing may be adapted to partially enclose the medicament delivery device.

In another embodiment, the compliance monitor housing may fully enclose and/or encircle, the medicament delivery device.

In one embodiment, the compliance monitor housing may be permanently attached to the medicament delivery device.

In another embodiment, the compliance monitor housing may be releasably attachable to, and/or around, the medicament delivery device.

In such an embodiment, any suitable releasable attachment means may be utilised.

For example, the compliance monitor housing may be provided with a hinged portion, which, when open, allows for the medicament delivery device to be placed within the compliance monitor housing, and which, when closed, serves to retain and/or enclose the medicament delivery device. The hinged portion may be provided with closure and release means, to secure the hinged portion, and release the hinged portion, respectively.

In another embodiment, the compliance monitor housing may be releasably attachable with respect to the medicament delivery device by an interference fit, a push fit, a slide-on fit, a clip on fit, a screw fit or a bayonette fit, sleeve, Velcro® or straps.

In another embodiment, the compliance monitor housing may be substantially U-shaped or tubular and designed to slide over and fit snugly onto the medicament delivery device.

In yet another embodiment, the compliance monitor housing may clip or adhere onto the surface of the medicament delivery device.

An advantage associated with having a releasably attachable compliance monitor housing is that the compliance monitor may be portable across a range of different medicament delivery devices and/or be reused by the patient.

The compliance monitor housing may be adapted to fit snugly to, on, or around, the medicament delivery device.

Alternatively, the compliance monitor housing may be loosely coupled with respect to the medicament delivery device.

The compliance monitor housing may preferably be attachable to, on, or around, the medicament delivery device, and subsequently operable, without any modifications being required to the medicament delivery device.

A significant advantage of such an arrangement is that the compliance monitor does not in any way interfere with, or otherwise affect, the ability of the medicament delivery device to administer medicament.

Preferably, the attaching of the compliance monitor housing to, on, or around, the medicament delivery device may not require the use of any tools; instead the medicament delivery device may be simply placed within, or otherwise attached to, the compliance monitor housing.

The compliance monitor housing may be made of any suitable material although a plastics material may be preferred as it is relatively light, and may be conveniently and inexpensively mass produced, for example by injection moulding technology.

Preferably, there may be a dose detection means associated with the compliance monitor, for determining when a dose of medicament has been dispensed.

Preferably, the dose detection means may be adapted to detect doses dispensed by the medicament delivery device, from a position outside of the medicament delivery device.

According to one aspect of the present invention, the dose detection means may be any electronic and/or mechanical dose detection mechanism.

Examples of suitable dose detection means, include (but are not limited to): a mechanical switch; an electromechanical switch; an electronic switch; an optical dose counter; a rotation detector; dose detection based on changes in pressure, temperature, acceleration or sound.

Such dose detection means or dose counters, for use with medicament delivery devices, are common to the prior art and will be well known by those skilled in the art, and it is not intended therefore to describe each in any great detail herein.

According to another aspect of the present invention, there is provided a compliance monitor, substantially as described above, wherein the recognition means includes:
a) a sensor,
b) an electronics control module (ECM) adapted to:
receive and process data from the sensor in order to identify the properties of the medicament delivery device,
compare the identified properties of the medicament delivery device with the properties of the prescribed medicament delivery device stored in the compliance monitor memory,
determine if the prescribed medicament delivery device is attached to the compliance monitor.

According to another aspect of the present invention, there is provided a compliance monitor, substantially as described above, wherein the ECM is further adapted to alert the user if an incorrect medicament delivery device is attached and/or to confirm that the correct medicament delivery device is attached.

According to another aspect of the present invention, there is provided a compliance monitor, substantially as described above, wherein the recognition means includes:
a) a sensor,
b) an electronics control module (ECM) adapted to:
receive data from the sensor,
transfer the data to a computing device external to the compliance monitor or the medicament delivery device, wherein the computing device is adapted to receive and process the data in order to identify the properties of the medicament delivery device, and subsequently compare the identified properties of the medicament delivery device with the properties of the prescribed medicament delivery device stored in the computing device memory, in order to determine if the prescribed medicament delivery device is attached to the compliance monitor.

In one embodiment, the computing device may be further adapted to alert the user if an incorrect medicament delivery device is attached and/or to confirm that the correct medicament delivery device is attached, including through display of the notification on the computing device (e.g. smartphone or web service) or on the user interface of the compliance monitor (LCD, LED, sound).

Preferably, the computing device external to the compliance monitor or medicament delivery device may include, without limitation, a mobile phone, a smartphone, an iPhone, an iPad, a tablet, a palmtop computer, a band or other wearable technology device, a small portable device, a laptop, a desktop computer, a remote network computer system (public network, e.g. a website, or private network) or to a web service, including, without limitation the web services platform described in our patent application No. US 2010/025028 Sutherland.

According to another aspect of the present invention, there is provided a compliance monitor, substantially as described above, wherein the sensor is an optical sensor.

In such an embodiment, the optical sensor may utilise any type of light from within the electromagnetic spectrum. For example, the optical sensor may utilise infrared light. Alternatively, the optical sensor may utilise visible light.

Any suitable properties of the medicament delivery device may be utilised for the purpose of being identified by the recognition means.

In one embodiment, the properties of the medicament delivery device being identified may be the light reflection properties of a surface of the medicament delivery device.

In another embodiment, the properties of the medicament delivery device being identified may be the IR wavelength reflection properties of a surface of the medicament delivery device.

In yet another embodiment, the properties of the medicament delivery device being identified may be the colour light reflection and/or absorption properties of a surface of the medicament delivery device.

Any surface of the medicament delivery device may be utilised for the purpose of enabling the recognition means to identify the properties of the medicament delivery device.

Preferably, an outer surface(s) of the medicament delivery may be utilised for the purpose of enabling the recognition means to identify the properties of the medicament delivery device.

For example, the outer surface may be the wall or base of a pMDI actuator, the base of a DPI or the wall of an injectable delivery device. In such embodiments, the outer surface of the medicament delivery device may be the outer surface of the store of the medicament or the outer surface of the housing which contains the store of the medicament.

According to another aspect of the present invention, there is provided a compliance monitor, substantially as described above, wherein the sensor is capable of identifying the properties of the medicament delivery device within a distance range of 0.1 mm-10 mm, and preferably in the range of 0.1 mm-5 mm.

According to another aspect of the present invention, there is provided a compliance monitor, substantially as described above, wherein the sensor includes:
a) at least one light emitter for transmitting light towards a surface of the medicament delivery device,
b) at least one light receiver for detecting the light after it has been reflected by the surface of the medicament delivery device.

In one embodiment, the light emitter may be adapted to emit a continuous beam of light. In another embodiment, the light emitter may be adapted to emit pulsed beams of light. In yet another embodiment, the light emitter may be adapted to emit both continuous beams of light and pulsed beams of light.

The light emitted by the light emitter may be visible light and/or invisible light.

Preferably, the light emitted by the light emitter may be non-visible light in the infrared light spectrum.

Any suitable light emitter, capable of emitting a beam of light, may be utilised. An example of a suitable light emitter is a LED, a blue, green or red light emitter, a laser, an IR emitter, or a visible light emitter.

Any suitable light receiver, capable of receiving and/or detecting the reflected beam of light may be utilised. An example of a suitable light receiver is a photodiode, a visible light receiver or a colour sensor chip.

According to another aspect of the present invention, there is provided a compliance monitor, substantially as described above, wherein the sensor further includes an integrated circuit which includes light emitter driving and light detecting circuits operably connected to the light emitter and light receiver.

According to another aspect of the present invention, there is provided a compliance monitor, substantially as described above, wherein the sensor is a matrix type sensor.

In such an embodiment, and for example, the matrix type sensor may be a digital image sensor such as a CCD chip sensor.

According to another aspect of the present invention, there is provided a compliance monitor, substantially as described above, wherein the axis of the light emitter is substantially parallel in relation to the axis of the light receiver.

According to another aspect of the present invention, there is provided a compliance monitor, substantially as described above, wherein the sensor further includes at least one lens adapted to refract the light emitted by the light emitter and/or the light to be received by the light receiver.

According to another aspect of the present invention, there is provided a compliance monitor, substantially as described above, wherein the light emitter is angled with respect to the light receiver.

According to another aspect of the present invention, there is provided a compliance monitor, substantially as described above, wherein the light emitter and the light receiver are angled toward each other.

In one embodiment, the angle between the axis of the light emitter and the axis of the light receiver may be between 40° to 120°.

Preferably, the angle between the axis of the light emitter and the axis of the light receiver may be approximately 60°.

Preferably, the axis of the light emitter and the axis of the light receiver may intersect at the surface of the medicament delivery device.

Preferably, the beam of light transmitted by the light emitter and the beam of light received by the light receiver may meet at the surface of the medicament delivery device.

Alternatively, the axis of the light emitter and the axis of the light receiver may not intersect at the surface of the medicament delivery device. However, in such an embodiment, the beam of light emitted by the light emitter and the beam of light received by the light receiver may nonetheless still meet at the surface of the medicament delivery device.

The light emitter and light receiver may preferably be angled and/or spaced apart at a distance that allows for light reflection from the medicament delivery device surface to be at a specified or desired height above the light emitter and light receiver. For example, the spacing and/or angles of the light emitter and light receiver may be determined from the target height of the medicament delivery device surface to be detected.

According to another aspect of the present invention, there is provided a compliance monitor, substantially as described above, wherein the reflected light received by the light receiver is converted into a corresponding voltage.

According to another aspect of the present invention, there is provided a compliance monitor, substantially as described above, wherein the size of the voltage generated is indicative of the colour or the wavelength signature of the medicament delivery device.

In one embodiment, the recognition means may have the ability to determine the colour of the medicament delivery device, by utilising commercially available colour sensors.

Furthermore, the recognition means may preferably be able to determine the colour of the medicament delivery device that is connected to the compliance monitor, and therefore be able to determine the type of medicament to be dispensed by the medicament delivery device.

Preferably, the recognition means may have the ability to determine and distinguish between the reflective properties of surfaces of different medicament delivery devices, based on the nature of the reflected light signal received by the light receiver.

Preferably, the recognition means may have the ability to distinguish between wavelength signatures of reflective as well as very non-reflective surfaces.

According to another aspect of the present invention, there is provided a compliance monitor, substantially as described above, wherein the ECM is further adapted to calculate and/or determine the colour or the wavelength signature of the medicament delivery device based on the nature of the reflected light and/or voltage generated.

Preferably, the reflected light signal received by the light receiver may be converted into a corresponding voltage, whereby the size of the voltage generated is determined by the nature of the reflected light signal. For example, the greater the voltage generated by the light receiver, the greater the intensity and/or brightness of the reflected light signal, and hence the greater the reflective properties of the surface of the medicament delivery device.

In such an embodiment, the ECM may further include an algorithm to make the determination.

In one embodiment, the sensor may be a proximity sensor and/or a colour sensor.

In such an embodiment, the proximity sensor may determine that the compliance monitor is correctly attached to the medicament delivery device.

In one embodiment, the ECM may be further adapted to detect the presence or absence of the medicament delivery device.

Preferably the sensor may be used for detecting the absence, or presence, of a medicament delivery device.

In such an embodiment the light emitter may be adapted to emit a beam of light towards the medicament delivery device, and the light receiver may be adapted to receive and/or detect the beam of light after it has been reflected from the medicament delivery device. The arrangement and construction may preferably be such that the sensor is able to detect the absence of the medicament delivery device when no reflected light is detected by the light receiver, and the sensor is able to detect the presence of the medicament delivery device when reflected light from the medicament delivery device is detected by the light receiver.

The compliance monitor may preferably be portable and/or releasably attachable to the medicament delivery device.

According to another aspect of the present invention, there is provided a compliance monitor, substantially as described above, wherein the medicament delivery device is a medicament inhaler further including:
 a) a housing to contain the store of medicament and
 b) a mouthpiece for directing the dose of medicament into the mouth of a user.

According to another aspect of the present invention, there is provided a compliance monitor, substantially as described above, wherein the compliance monitor further includes a wireless communication means, for the wireless transmission of usage data to a computing device external to the compliance monitor or medicament delivery device.

Preferably the compliance monitor may include some or all of the common features associated with such presently available devices, including, without limitation, a user interface (with at least one operational button(s) and/or an LCD screen), a battery, and/or audio/visual notification means to notify or remind the patient of a particular event. The user interface may be used to access data recorded or received by the compliance monitor and also change the settings of the compliance monitor (for example, date/time, visual/audio alert setting). The user interface may also be used to access any data received (or transmitted) by the compliance monitor or to control the upload of the data from the compliance monitor to a computing device external to the compliance monitor or medicament delivery device.

Preferably, the compliance monitor may include a memory for the storage of data.

In some embodiments, a volatile type computer memory, including RAM, DRAM, SRAM, may be used. In such instance, the compliance monitor may continually transmit information to the computing device external to the compliance monitor or medicament delivery device.

In other embodiments non-volatile memory formats may be used, including ROM, EEPROM, flash memory, ferroelectric RAM (F-RAM), optical and magnetic computer memory storage devices, and others.

Preferably, the compliance monitor includes communication means. The communication means may be in electronic communications with the ECM and either a stand alone component, or part of the ECM. The communication means may include a wired and/or wireless link. Any suitable wireless technology known in the art may be used, including Wi-Fi (IEEE 802.11), LE Bluetooth®, Bluetooth®, other radio frequencies, Infra-Red (IR), GSM, CDMA, GPRS, 3G, 4G, W-CDMA, EDGE or DCDMA200 and similar technologies. Any suitable wired connections or ports may be used, including, without limitation USB ports or any other technology known in the art.

Preferably, the ECM may be configured to cause the communication means to transfer and/or receive data to/from a computing device external to the compliance monitor or the medicament delivery device.

Preferably the compliance monitor may be paired with a smart phone loaded with a software application which allows the smart phone to access, process, and present the data collected.

Preferably, the smart phone may be configured to transfer the data obtained from the compliance monitor to a web services platform.

According to another aspect of the present invention, there is provided a method for identifying a medicament delivery device associated with a compliance monitor, said method including the steps of:
a) identifying the properties of the medicament delivery device using a recognition means associated with the compliance monitor;
b) comparing the identified properties of the medicament delivery device with the known properties of the prescribed medicament delivery device,
c) determining if the prescribed medicament delivery device is connected to the compliance monitor.

Preferably, the method may further include the step of notifying the user of the result of the determination via a user interface associated with the compliance monitor and/or transmission of the result of the determination to a computing device external to the compliance monitor.

In one embodiment of the present invention, the notification may be a confirmation that the medicament delivery device connected to the compliance monitor is as prescribed by the user's health care professional.

In another embodiment of the present invention, the notification may be an alert that an incorrect medicament delivery device is connected to the compliance monitor.

In yet another embodiment of the present invention, the notification may be a notification that no medicament delivery device is connected to the compliance monitor.

According to another aspect of the present invention there is provided an optical sensor including:
a) an IR light emitter and an IR light receiver, wherein the axis of the light emitter is substantially parallel to axis of light receiver;
b) a first portion, consisting of a base, which houses the IR light emitter, IR light receiver and an IR divider which separates the IR light emitter from the IR light receiver;
c) a second portion consisting of a moulded cover which fits over the first portion; the arrangement and construction being such that the part of the second portion that fits above the IR emitter or IR receiver is moulded as a lens, and wherein:
  (i) each lens has a shape of a triangular prism, the vertical axis of which is rotated 90° away from the IR divider, and the base of which is cut off on an angle to allow the base to abut to the side of the IR divider;
  (ii) the lens positioned over the light emitter is adapted to refract the beam of emitted light by approximately 10° to 40°;
  (iii) the lens positioned over the light receiver is adapted to refract the reflected light beam by approximately 10° to 40°.

The optical sensor may preferably be configured to detect objects at distances from 0.1 mm to 5 mm.

According to another aspect of the present invention, there is provided an optical sensor, substantially as described above, wherein the optical sensor is fitted into a compliance monitor.

PREFERRED EMBODIMENTS

The description of a preferred form of the invention to be provided herein, with reference to the accompanying drawings, is given purely by way of example and is not to be taken in any way as limiting the scope or extent of the invention.

DRAWINGS

Figure 2:
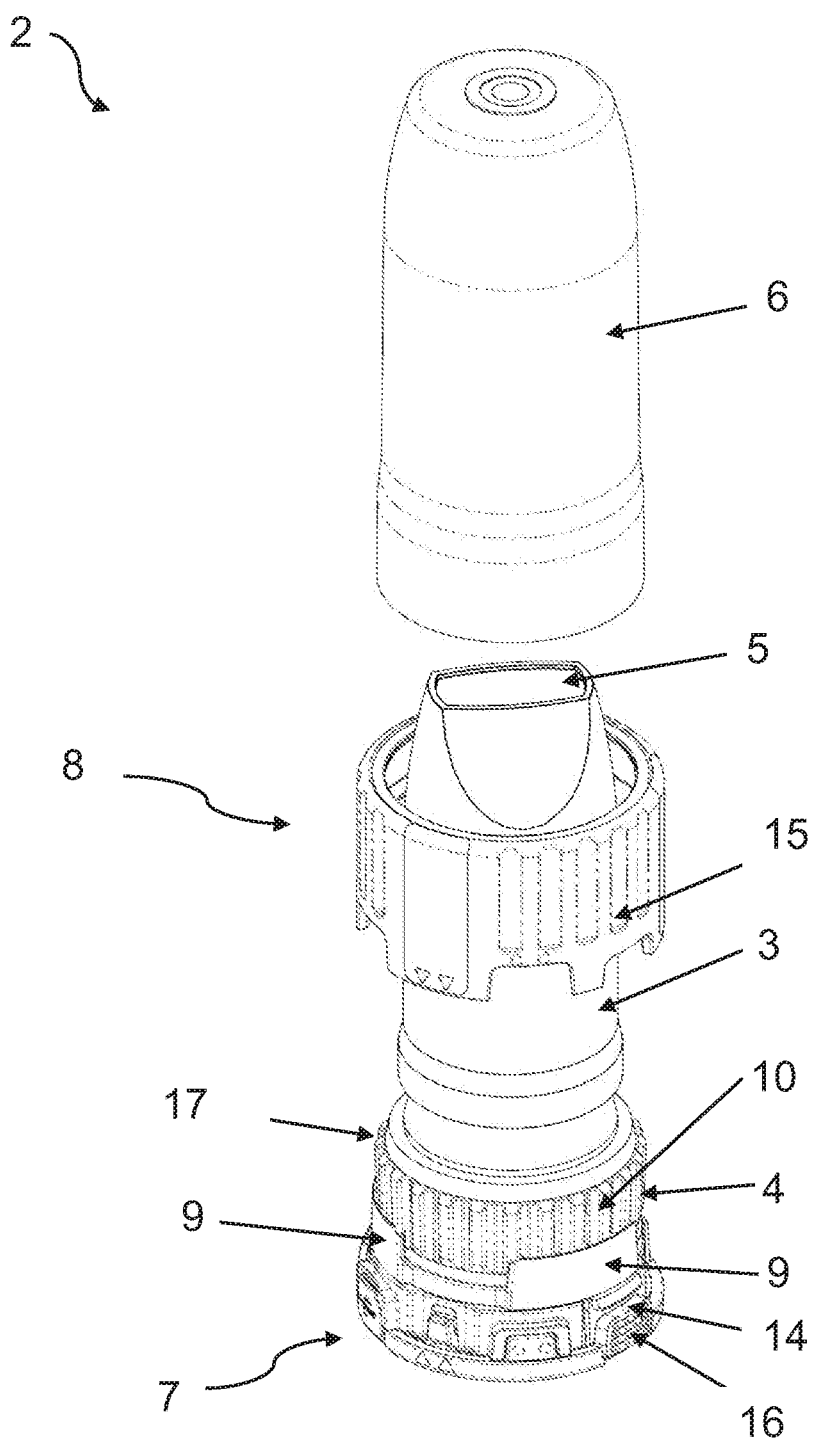
Figure 3:
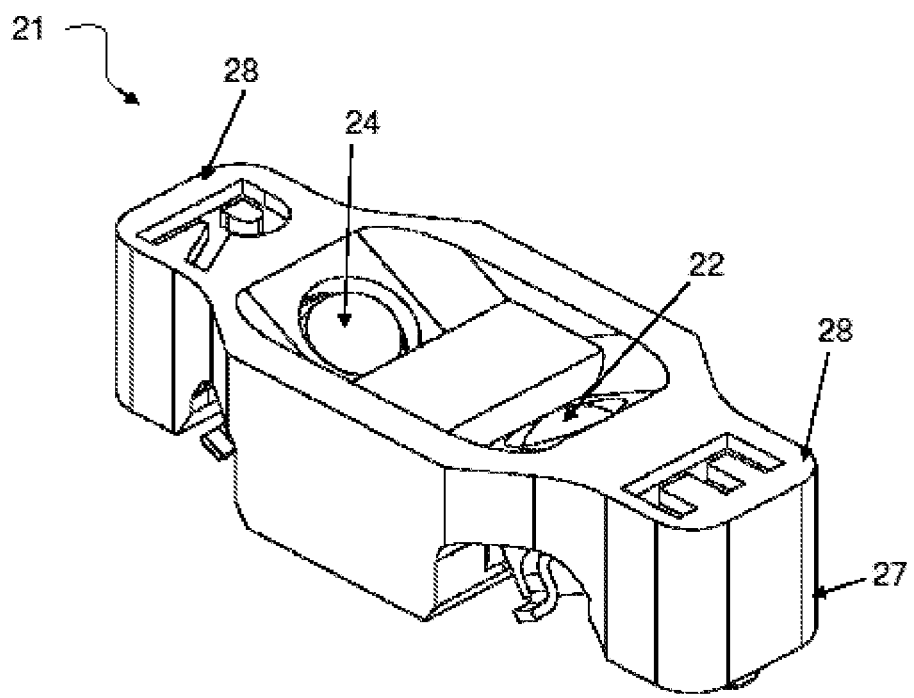
Figure 4:
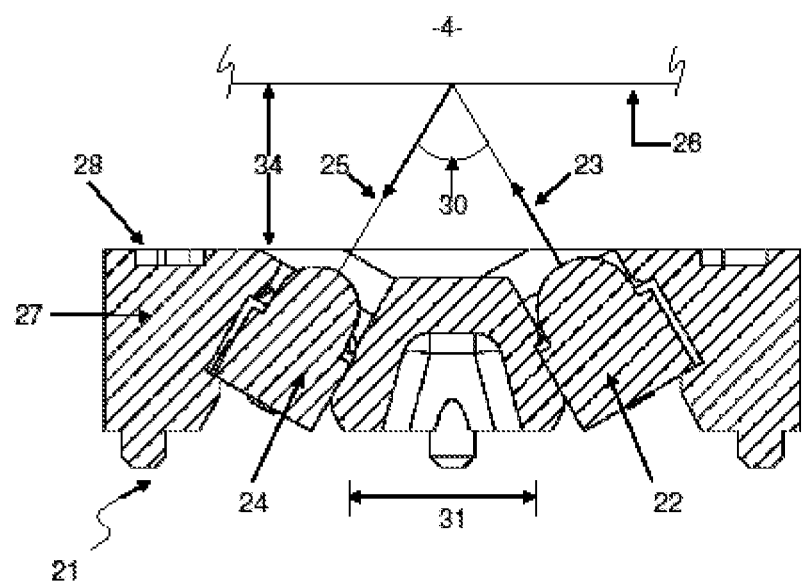
Figure 5:
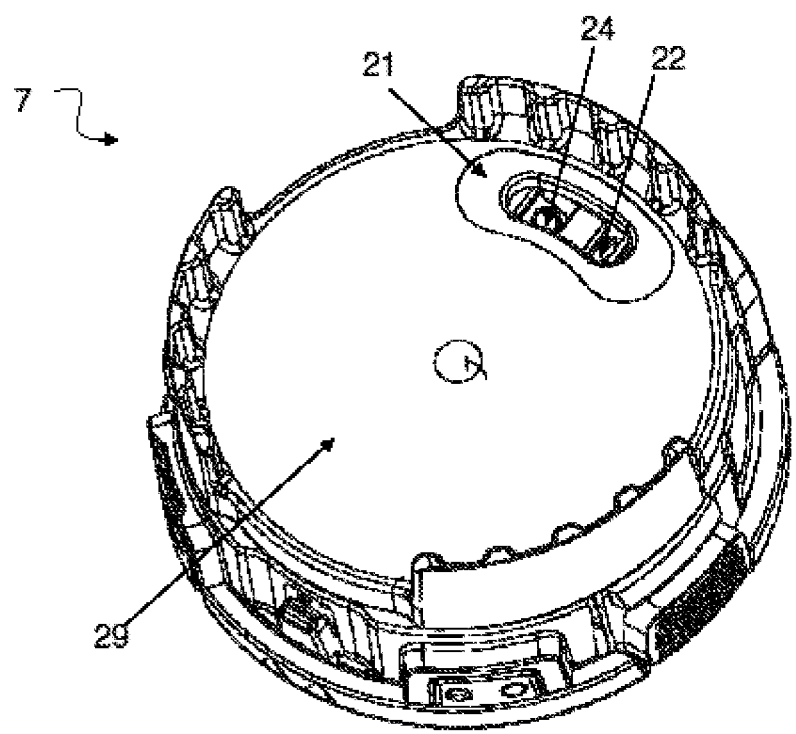
Figure 7A:
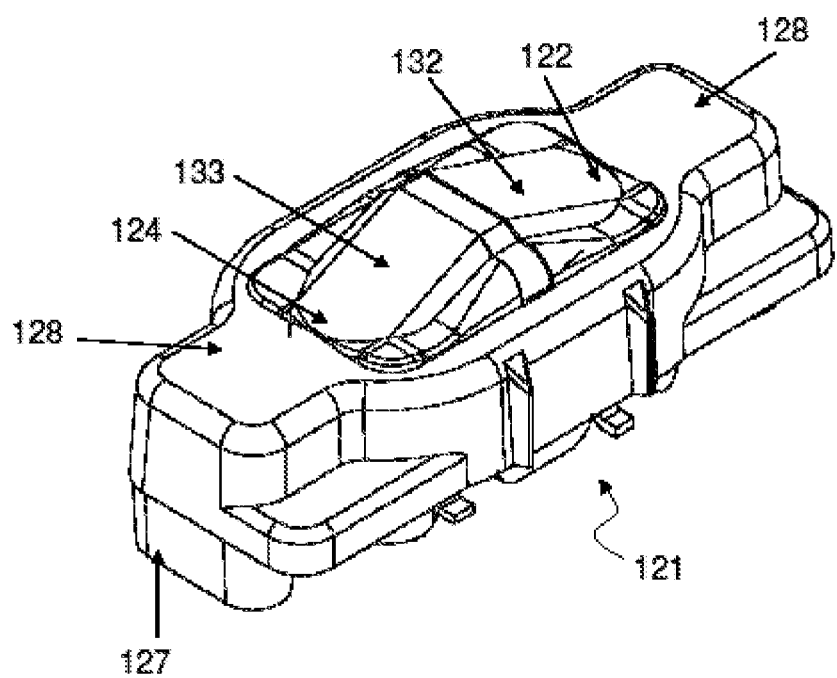
Figure 7B:
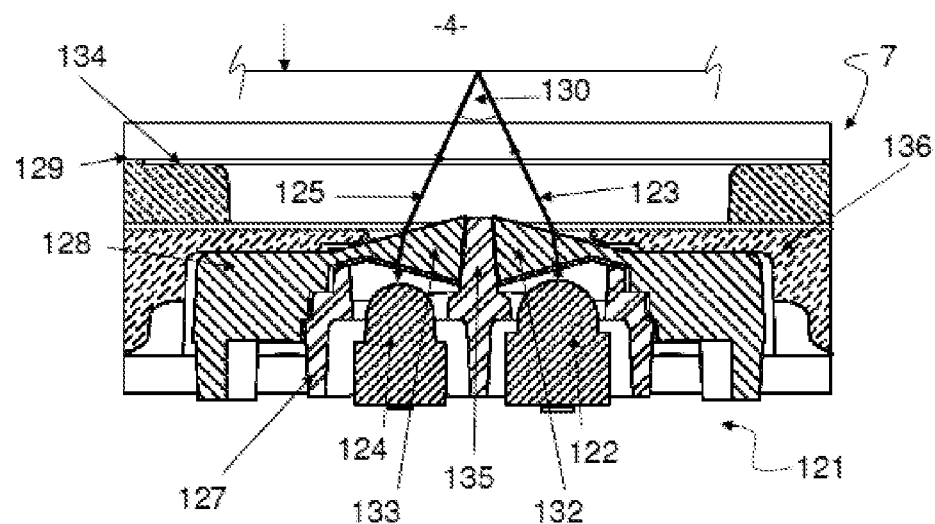
Figure 7C:
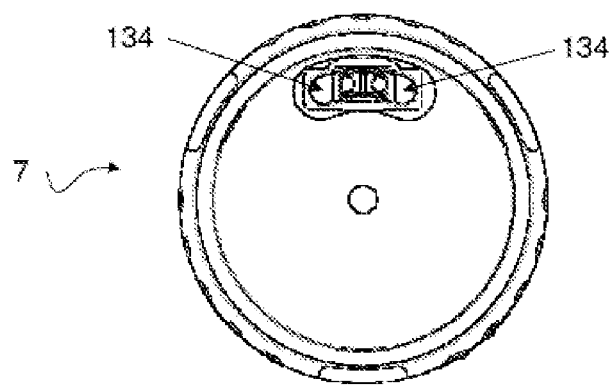
Figures 8A, 8B:
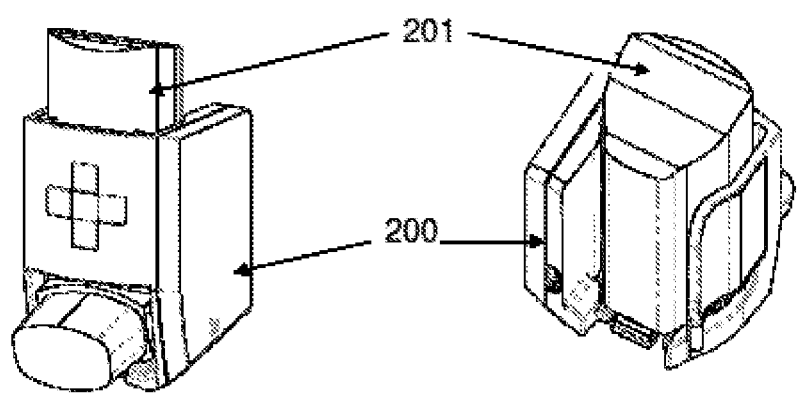
Figures 8C, 8D:
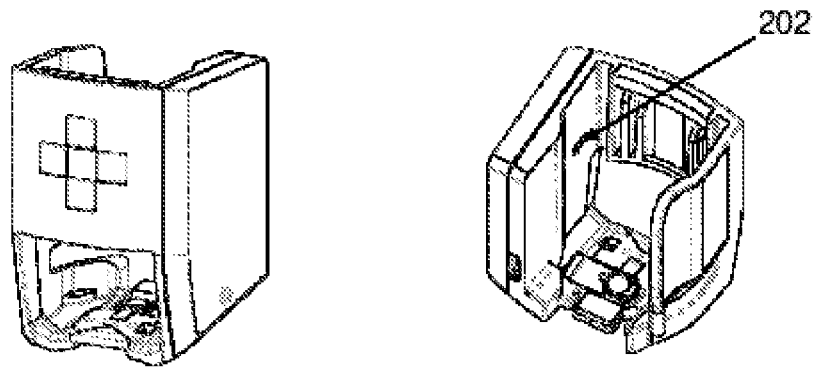

FIG. 1: is an exploded view of a prior art compliance monitor, used for monitoring patient usage of a dry powder medicament delivery device, FIG. 2: is a view of the prior art compliance monitor illustrated in FIG. 1, when fitted to a dry powder medicament delivery device, FIG. 3: is a perspective view of one possible embodiment of a sensor for use with a compliance monitor, FIG. 4: is a cross-sectional side view of the sensor illustrated in FIG. 3, FIG. 5: is a view of the sensor illustrated in FIGS. 3 and 4, when fitted to the compliance monitor illustrated in FIGS. 1 and 2, FIGS. 6A & 6B: are flowcharts representing possible embodiments of the process of medicament delivery device identification and generation of a confirmation or alert by a compliance monitor including a recognition means in relation to: (6A) TURBUHALER® inhalers; (6B) an unspecified range of medicament delivery devices;

FIG. 7A: is a perspective view of another possible embodiment of a sensor for use with the compliance monitor;

FIG. 7B: is a cross-sectional side view of the sensor illustrated in FIG. 7A;

FIG. 7C: is a planar view of the top of the compliance monitor for dry powder medicament delivery device illustrated in FIG. 5 fitted with the sensor illustrated in FIGS. 7A and 7B, FIGS. 8A-8D: are perspective views of a prior art pMDI compliance monitoring device. FIG. 8D shows the prior art pMDI compliance monitor and the position where the sensor is fitted.

DESCRIPTION OF PREFERRED EMBODIMENTS

Embodiment 1: DPI Compliance Monitor with Recognition Means Using an Angled Mount IR Sensor Having regard to FIGS. 1 and 2, there is shown a prior art compliance monitor, generally indicated by arrow 1, for use in monitoring patient usage of a dry powder inhaler, generally indicated by arrow 2. The dry powder inhaler 2 is a TURBUHALER®, which is manufactured and marketed by AstraZeneca AB.

The compliance monitor 1 and inhaler 2 are described in our NZ Patent No. 622000 Sutherland, and the contents of that patent specification are thereby incorporated herein by reference.

A brief summary of the main features and workings of the compliance monitor 1 and inhaler 2, as described in NZ 622000 Sutherland, now follows.

The inhaler 2 includes a store of medicament (not shown) which is housed within a main body portion 3. The inhaler 2 also includes a rotatable base portion 4, which is rotatable with respect to the main body portion 3. The inhaler 2 also includes a mouthpiece 5, through which a dose of medicament may be inhaled by a user. Also included is a removable and replaceable cap 6.

The compliance monitor 1 includes a first portion 7 for receiving and retaining the base portion 4 of the inhaler 2.

The compliance monitor 1 also includes a second portion 8 for releasably securing the inhaler 2 to the first portion 7, thereby releasably attaching the compliance monitor to the inhaler 2.

The arrangement and construction is such that the fitting of the second portion 8 of the compliance monitor 1 to the first portion 7 of the compliance monitor 1 includes a push fit.

The compliance monitor 1 may be attached to the inhaler 2 as follows:

Firstly, the cap 6 is removed from the inhaler 2.

Secondly, the base portion 4 of the inhaler 2 is placed within the first portion 7 of the compliance monitor 1. The base portion 4 is located by, and/or retained within, the first portion 7 by the upwardly projecting flanges 9.

Furthermore, the base portion 4 includes external serrations 10, and the interior surfaces of the flanges 9 contain complimentary serrations 11. These serrations 10, 11 interlock with each other, whereby rotation of the first portion 7 also causes a like rotation of the base portion 4.

That is, the first portion 7 and the base portion 4 move (rotate) as one.

Once the base portion 4 has been placed within the first portion 7, the second portion 8 of the compliance monitor 1 may then be fitted to the first portion 7 as indicated by the alignment means 12 to thus releasably attach the compliance monitor 1 to the inhaler 2. This is achieved by placing the second portion 8 over the mouthpiece 5, and sliding the second portion 8 down towards the first portion 7, as illustrated in FIG. 2.

The first portion 7 includes two clips 14, which are formed on substantially opposite sides of the first portion 7 (only one clip 14 is shown in FIGS. 1 and 2). As the second portion 8 is slid down and engaged with the first portion 7, each clip 14 clips into a corresponding retaining slot (not shown) formed on the inside surface of the second portion 8, in the region indicated by arrow 15. Once the clips 14 have engaged with these slots, the first and second portions are thus (releasably) connected, and the compliance monitor 1 is thereby (releasably) attached to the inhaler 2.

The first portion 7 of the compliance monitor 1 also includes a quick release means 16 (only one is shown) to enable the removal of the second portion 8 from the first portion 7.

The engagement of the clips 14 with the retaining slots may (optionally) serve as a device detection means, for example by closing an electronic circuit, to thus record that the compliance monitor 1 is attached to the inhaler 2.

Likewise, the disengagement of the clips 14 from the retaining slots may (optionally) open the same electronic circuit to thus record that the compliance monitor 1 has been removed from the inhaler 2.

The inside of the second portion 8 includes a sliding clip 13, which is illustrated in exploded view in FIG. 1. The sliding clip 13 is able to slide up and down within the inside of the second portion 8 (with approximately 2-5 mm total movement possible). Clip 13 forms part of the cap detection system as previously described.

The compliance monitor 1 includes dose detection means for determining if a dose of medicament has been dispensed and/or if the base portion 4 has been rotated with respect to the main body portion 3.

Furthermore, the compliance monitor 1 is electronic and includes an electronics control module (ECM), with the ECM being adapted to monitor and/or manipulate and/or store and/or transmit all compliance data gathered, relating to the patient usage of the inhaler 2 (ECM not shown).

Having regard to FIGS. 3 and 4, there is shown one example of a sensor for identifying the properties of the inhaler 2.

In this embodiment, the sensor is an optical sensor, generally indicated by arrow 21, which may be used for identifying the properties of a medicament delivery device, such as the inhaler 2. In this instance, the properties being identified and/or determined relate to the infrared light reflection properties of the outer surface of the base portion 4 of the inhaler 2, as illustrated in FIGS. 1 and 2.

The sensor 21 includes a light emitter 22 for emitting a beam of light 23 towards the underside 26 of the base portion 4. The sensor 21 further includes a light receiver 24, for receiving and/or detecting the reflected beam of light 25 after it has been reflected from the underside 26 of the base portion 4 (see FIG. 4).

It may be appreciated that the sensor 21 may detect the absence of the base portion 4 (and therefore the inhaler 2) when no reflected light 25 is detected by the light receiver 24. Furthermore, the sensor 21 may detect the presence of the base portion 4 (and therefore the inhaler 2) when reflected light 25 from the base portion 4 is detected by the light receiver 24.

In this example, the light emitter 22 is a LED, adapted to emit a continuous beam of light in the (invisible) infrared light spectrum. Furthermore, the light receiver 24 is a photodiode adapted to receive and/or detect any reflected infrared light emitted by the light emitter 22.

The sensor 21, including the light emitter 22 and light receiver 24, may be housed within an injection moulded plastic housing 27.

In this example the housing 27 is adapted to be incorporated within the first portion 7 of the compliance monitor 1, as illustrated in FIG. 5. The housing 27 may be fixed or removable with respect to the first portion 7 of the compliance monitor 1.

The top surface 28 of the housing 27 is recessed approximately 1 mm below the surface 29 of the first portion 7. During the rotation of the base portion 4 of the inhaler 2, when fitted to the compliance monitor 1, the base portion 4 may be elevated slightly off the surface 29. Hence, the distance 34 between the top surface 28 of the housing 27 and the underside 26 of the base portion 4 (of the inhaler 2) is approximately 2.2 mm.

The light emitter 22 and the light receiver 24 are spaced apart and angled towards each other, at a suitable distance and angle, whereby the reflected light signal 25 (reflected from the underside 26 of the base portion 4) is able to be received and/or detected by the light receiver 24. That is, the spacing and/or angles of the light emitter 22 with respect to the light receiver 24 are primarily determined from the target height of the base portion 4 to be detected. The positioning of the light emitter and light receiver in relation to each other and the base of the inhaler is important. It determines the angle of incidence and angle of reflection and maximises the efficacy of the recognition means to detect specular or speckle reflection of the light beam off a non-reflective surface.

In the embodiment shown, the angle 30 between the axes 23 and 25 of the light emitter 22 and light receiver 24 respectively is approximately 60°. Furthermore, the distance 31 between the closest edges of the light emitter 22 and the light receiver 24 is approximately 3.4 mm (drawing not to scale).

The recognition means including the sensor 21 and an ECM (not shown) is adapted to determine the light reflecting properties, in this embodiment, the IR wavelength reflection signature of the object being detected (base portion 4 of inhaler 2), based on the nature of the reflective surface and the reflected light signal 25 received by the light receiver 24. That is, the nature of the reflected light signal 25 will be influenced by the reflective and/or absorption properties of the surface of the base portion 4.

The reflected light signal 25 received by the light receiver 24 is converted into a corresponding voltage or output, whereby the size of the voltage or output generated is determined by the nature of the reflected light signal 25, e.g., the intensity and/or brightness of the reflected light signal 25.

Each base portion 4 will have its unique IR wavelength signature. The voltage or output generated by a base portion 4 of a specific type can be recorded in the ECM associated with the sensor and used as a reference in differentiating between different base portions (and therefore different inhalers 2).

In the present case of the recognition means using IR wavelength, the output may additionally and/or alternatively depend on the properties of the material used in the manufacturing of the base (i.e., the output may not be determined purely by the colour of the inhaler surface). The type of plastic and pigments used in manufacturing alter the reflectivity and/or absorption properties of the inhaler surfaces. For example, in the case of the TURBUHALER® inhalers, the bases are made using linear low-density polyethylene (LLDPE).

ECM compares the output generated by the IR receiver against a table of readings specific to the different base portions in the medicament delivery device category, for example a table of output readings for all TURBUHALER® inhalers available on the market.

For each type of surface to be detected, the ECM can thus be calibrated to associate certain levels of voltage or output with different medicament delivery devices. For example, in the case of TURBUHALER® inhalers, the recognition means may be calibrated as follows:

| Light Receiver output (%) | Reading |
| --- | --- |
| 0-2% | No inhaler detected |
| 3-25% | Inhaler detected/Inhaler ID: Plumicort ®(AstraZeneca) |
| 25-35% | Inhaler detected/Inhaler ID: Symbicort ® (AstraZeneca) |
| 35-50% | Inhaler detected/Inhaler ID: Bricanyl ® (AstraZeneca) |
| 60-80% | Inhaler detected/Inhaler ID: Clinical trial use Turbuhaler ® (white base) |

It should be noted that in the above embodiment, a light receiver output of 0-2% (meaning no object detected) would also be recorded if the compliance monitor 1 were placed upside down on a surface (as often happens when the compliance monitor 1 is not currently fitted to an inhaler 2).

For other ranges of medicament delivery device surfaces to be detected and identified using the compliance monitor of the present invention, the recognition means may be recalibrated (through earlier testing and subsequent ECM programming) to assign lower, higher or different ranges of output percentages to each surface in the range.

Figure 6A:
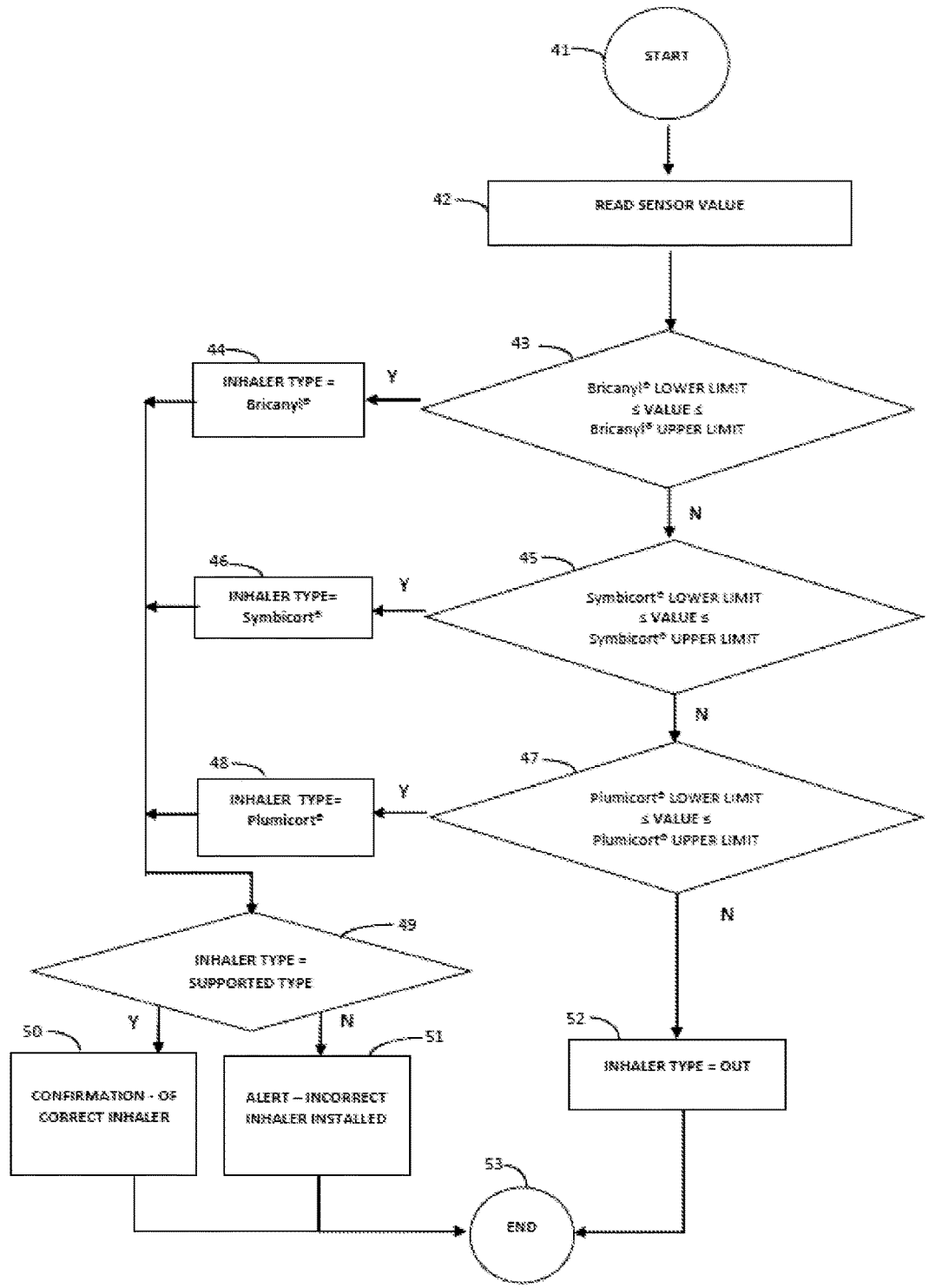
Figure 6B:
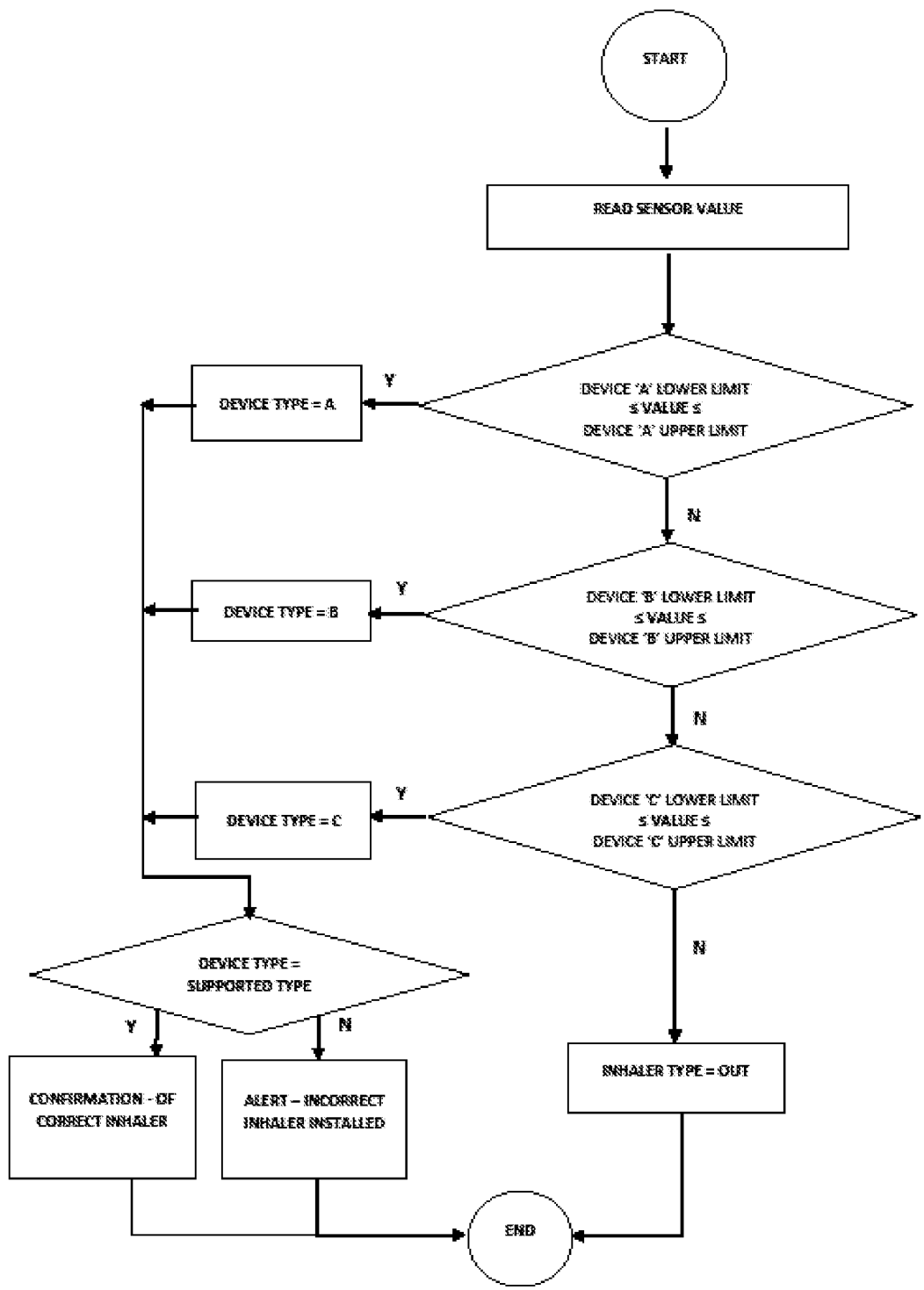

FIGS. 6A and 6B illustrate, without limitation, two examples of the process and method through which the data relating to the properties of the medicament delivery device may be processed. FIGS. 6A and 6B are only given by way of example and other available methods may also be implemented.

In one example of the invention, the process may commence following a mechanical or timed trigger 41. For example, the ECM, connected with the sensor 21, may be activated when the second portion 8 of the compliance monitor 1 shown in FIGS. 1 and 2 is fitted into the first portion 7 (with or without inhaler 2 present). The ECM may activate the sensor 21 which will emit and receive the IR light signal. The output of the photoresistor (photodiode) may be converted by A/D converter and read by the ECM at step 42. If a colour sensor chip is used as the sensor, the output may be read directly without A/D converter.

In some embodiments, the output value read may be compared against the expected limits of output ranges indicative of the inhaler 2 being installed into the compliance monitor (not shown). If the value read falls within the 'inhaler in' range, the ECM detects the presence of the inhaler 2, updates the status, stores 'medication in" log (not shown).

The read output value is compared against a table of output values associated with a family of medicament delivery devices (at steps 43, 45, 47) which fit into the given compliance monitor. For example, as illustrated in FIG. 6A, if the output value read by ECM is greater than the lower limit and lower than the upper limit of the output value generated by base portion 4 of a Bricanyl® TURBU-HALER® at step 43, the ECM recognises the device at step 44, and the next decision point is whether the inhaler detected is in fact supported at step 49 by the compliance monitor. The information as to which device is supported is embedded in the memory of the ECM (e.g., ROM). If Bricanyl® TURBUHALER® is the supported inhaler, the ECM signals to the user interface a confirmation of the correct inhaler being installed at step 50. If Bricanly® is not supported, ECM causes an alert to be issued that an incorrect device was installed at step 51.

If the value read does not match with the value for devices coded as "Blue/Green', the values read are compared to the remaining ranges (at steps 45 and 47) until a match is found (at step 46 or 48). If no match is found, the ECM updates the status and logs 'medication out' at step 52.

The same process may be followed for other medicament delivery devices which are differentiated purely by their surface properties, e.g. some injectable delivery devices. As illustrated by FIG. 6B, the ECM may be configured to distinguish between properties of 2 or more devices, as long as each of the devices can be characterised by different reflective properties using any sensor available.

Alternatively, the data received from the sensor may be transferred (e.g., by a wireless communicator) to a computing device external to the compliance monitor or the medicament delivery device. In such an embodiment the computing device may be adapted to receive and process the data in order to identify the properties of the medicament delivery device, and subsequently compare the identified properties of the medicament delivery device with the properties of the prescribed medicament delivery device stored in the computing device memory, in order to determine if the prescribed medicament delivery device is attached to the compliance monitor.

The sensor 21 is in electronic communication with the ECM of the compliance monitor 1, whereby the data gathered and/or the determinations made by the sensor may be communicated to the ECM.

The compliance monitor 1 is thus able to detect the absence or presence of the inhaler 2 (or more correctly the base portion 4 of the inhaler 2), as well as being able to identify what base portion 4 of the inhaler 2 is detected, and this compliance data may thus be recorded by the ECM, along with all other compliance data gathered (such as dose detection and so on).

Furthermore, the ECM of the compliance monitor 1 may include data regarding what type of medicament should be taken by the patient, and at what time.

Hence, the ECM is able to determine if a patient places an incorrect medicament into the compliance monitor 1 (and/or at an incorrect time), based on the determination of the identity of the base portion 4 of the inhaler 2—by the sensor 21. This data may simply be recorded whereby it may be reviewed and/or assessed later (either by the patient or a healthcare professional). Alternatively and/or additionally, an audible and/or visual alert may be automatically triggered by the compliance monitor 1 to warn the patient that an incorrect medicament has been (or is about to be) used.

For example, if the sensor 21 detects the presence of a blue coloured base portion 4 (a reliever medicament such as Bricanyl® TURBUHALER®) within the compliance monitor 1, whereas at that time, and according to that patient's treatment regime, a brown-coloured preventer medicament (such as Plumicort® TURBUHALER®), was meant to have been taken by the patient, then an alert may be sounded to warn of the patient of his/her mistake. Furthermore, this data will be recorded by the ECM, so that a healthcare professional will be aware of such errors when reviewing the data at a later date. Hence, the healthcare professional may look to remind or retrain the patient regarding his/her use of the different medicaments.

In the example provided above, it is feasible that the patient intended to use the reliever medicament instead of the preventer medicament due to an exacerbation event such as an asthma attack. However, in such a scenario, the healthcare professional is nonetheless still alerted to the fact that a reliever medicament has been used and/or that an exacerbation event may have occurred. This is important, as the healthcare professional may then look to review the treatment regime of that patient, based on the number or frequency of exacerbation events occurring.

Embodiment 2: DPI Compliance Monitor with Recognition Means Using an Optical Sensor Having regard to FIGS. 7A-7C, there is shown another embodiment of a sensor 121. The axes of the light emitter 122 and light receiver 124 are parallel. The sensor 121 further includes:

(a) first portion 127, consisting of a base which houses the IR light emitter 122, the IR light receiver 124 and an IR opaque divider 135 which separates the IR emitter 122 from the IR receiver 124 and blocks a portion of the cross-talk between the emitter 122 and the receiver 124, and (b) the second portion 128 consisting of a IR transparent moulded cover which fits over and covers the first portion 127.

The second portion 128 is moulded to create a first lens 132 positioned above the light emitter 122, and a second lens 133 positioned above the light receiver 124. The first lens 132 and second lens 133 have the form of a triangular prism, the vertical axis of which is rotated 90° away from the IR divider 135. The base of each lens 132, 133 is cut off on an angle to abut to the sides of the IR divider 135.

FIG. 7A is a perspective view of the sensor 121 with the IR light emitter 122, the IR light receiver 124 and an IR opaque divider 135 covered by the second portion 128.

FIG. 7B is a cross-sectional view of the sensor 121. As illustrated on FIG. 7B the first lens 132 is adapted to refract the beam of light 123 being emitted by the light emitter 122 by a total of approximately 20°. Likewise, the second lens 133 is adapted to refract the reflected beam of light 125 by a total of approximately 20°, the arrangement and construction being such that the reflected beam of light 125 is thus directed into or towards the light receiver 124. The angle 130 in FIG. 7 is therefore approximately 40°.

As can be seen in FIG. 7B, the emitted beam of light 123 is refracted twice by the first lens 132—once as it enters the bottom of the first lens 132, and again as it exits from the top of the first lens 32. Likewise, the reflected beam of light 125 is refracted twice by the second lens 133—once as it enters the top of the second lens 133, and again as it exits the bottom of the second lens 133.

It may be appreciated therefore that the lenses 132, 133 serve substantially the same purpose as having the light emitter 122 angled with respect to the light receiver 124 as illustrated in the embodiments in FIGS. 4 and 5. That is, the effect or functionality created by having the light emitter 122 and light receiver 124 angled towards each other is instead achieved, or replicated, by the use of the refractive properties of the first lens 133 and second lens 134.

As illustrated by FIGS. 7B and 7C, the sensor may be further adjusted to remove cross-talk between the IR emitter 122 and IR receiver 124, by means of providing additional IR opaque shroud 136 above the sensor 121. FIGS. 7B and 7C illustrate how the sensor 121 may be fitted into the DPI compliance monitor shown in FIGS. 1, 2 and 5. The first portion 7 of the DPI compliance monitor 1 is adapted to incorporate the sensor 121. The sensor 121 is recessed below the surface 129 of the first portion 7. A portion of the sensor 121 is covered by a shroud 136 and the sensor 121 may additionally be covered by an IR transparent cover 134. The base portion 4 of the inhaler 2 rests above when fitted to the compliance monitor 1, that is, it is elevated slightly off the surface 129 of the first part 7 of the compliance monitor.

The sensor 121 is connected to an ECM (not shown) also embedded in the first portion 7 of the compliance monitor 1. The same identification processes as described above are applicable to recognition means using sensor 121.

Embodiment 3: pMDI Compliance Monitor with Recognition Means Using an Optical Sensor Another embodiment of the compliance monitor of the present invention is illustrated in FIGS. 8A-8D. FIGS. 8A-8D show perspective views of a prior art compliance monitor, generally indicated by arrow 200, for use in monitoring patient usage of a pressurised metered dose inhaler (pMDI), generally indicated by arrow 201. The compliance monitor 200 is a loosely coupled pMDI compliance monitor as described in our patent application No. WO 2013/043063 Sutherland, and the contents of that patent specification are thereby incorporated herein by reference.

Having regard to FIGS. 8A and 8B, there is shown Ventolin® pMDI. Briefly, the compliance monitor shown in FIGS. 8A-8D includes: a housing adapted to enclose the medicament delivery device, a dose counter associated with the housing for recording a delivery of a dose of medicament to the patient from the medicament delivery device. The arrangement and construction is such that the housing is loosely coupled to the medicament delivery device, whereby the housing is able to move relative to the medicament delivery device during the delivery of the dose of medicament, and it is this movement which actuates the dose counter, either directly or indirectly.

Having regard to FIG. 8D, there is shown the position of the sensor 202 which is part of the recognition means associated with the loosely coupled compliance monitor 200.

Any suitable sensor 202 may be used. The sensor 202 is connected to an ECM (not shown) also embedded in the compliance monitor 200. The same identification process as described above is applicable.

The compliance monitors and the methods of the present invention are also suitable for identification of DPI inhalers in the form of a disc (e.g., Accuhaler® or Diskus® by GlaxoSmithKline). For example, a recognition means can be fitted into a U-shaped compliance monitor disclosed in our patent application No. US2014/0000598 (Sutherland).

The compliance monitors and the methods of the present invention are also suitable for identification of injectable delivery devices. For example, in case of insulin-specific injectable delivery devices, a compliance monitor of the present invention may take a form of a thin tubular push-on or clip on device fitting over a portion of the injectable delivery device. Such compliance monitor may utilise sensors described above. In another embodiment, such compliance monitor may include a recognition means that utilises sensors wherein at least one, and preferably more than one, light emitters are placed opposite matching light receivers with both the emitters and the receivers placed along the length of the inner wall of the compliance monitor encompassing an injectable delivery device. In cases of injectable delivery devices translucent to visible light (or IR translucent, if IR emitters and receivers are used) the recognition means may be calibrated to detect the levels of injectable medicament in the injectable delivery device and fulfil the function of a dose detection means.

Variations

While the embodiments described above are currently preferred, it will be appreciated that a wide range of other variations might also be made within the general spirit and scope of the invention, and/or as defined by the appended claims.

We claim:

1. A compliance monitor for monitoring usage and type of a medicament delivery device, the medicament delivery device including a store of medicament, and a medicament dispenser for delivering a dose of medicament, the compliance monitor comprising:
    a compliance monitor housing configured to attach to the medicament delivery device,
    a dose detector for determining when a dose of medicament is dispensed, and
    a recognition module including an infrared light sensor configured to identify properties of the medicament delivery device, wherein the identified properties of the medicament delivery device include a type of plastic material, the type of plastic material being indicative of the type of medicament delivery device.

2. The compliance monitor as claimed in claim 1, wherein the recognition module includes:
    an electronics control module (ECM) configured to:
        receive and process data from the sensor in order to identify the properties of the medicament delivery device,
        compare the identified properties of the medicament delivery device with the properties of the prescribed medicament delivery device stored in the compliance monitor memory, and
        determine if the prescribed medicament delivery device is attached to the compliance monitor.

3. The compliance monitor as claimed in claim 1, wherein the recognition module includes an electronics control module (ECM) configured to:
    receive data from the sensor, and
    transfer the data to a computing device external to the compliance monitor or the medicament delivery device, wherein the computing device is configured to receive and process the data in order to identify the properties of the medicament delivery device, and subsequently compare the identified properties of the medicament delivery device with the properties of the prescribed medicament delivery device stored in the computing device memory, in order to determine if the prescribed medicament delivery device is attached to the compliance monitor.

4. The compliance monitor as claimed in claim 2, wherein the ECM is further configured to alert the user if an incorrect medicament delivery device is attached and/or to confirm that the correct medicament delivery device is attached.

5. The compliance monitor as claimed in claim 2, wherein the sensor is an optical sensor.

6. The compliance monitor as claimed in claim 1, wherein the properties of the medicament delivery device being identified include the IR wavelength reflection properties of a surface of the medicament delivery device.

7. The compliance monitor as claimed in claim 1, wherein the properties of the medicament delivery device being identified are determined from an outer surface of the medicament delivery device.

8. The compliance monitor as claimed in claim 1, wherein the sensor is capable of identifying the properties of the medicament delivery device within a distance range of 0.1 mm-5 mm.

9. The compliance monitor as claimed in claim 1, wherein the sensor includes:
at least one light emitter for transmitting light towards a surface of the medicament delivery device, and
at least one light receiver for detecting the light after it has been reflected by the surface of the medicament delivery device.

10. The compliance monitor as claimed in claim 9, wherein the sensor further includes an integrated circuit which includes light emitter driving and light detecting circuits operably connected to the light emitter and light receiver.

11. The compliance monitor as claimed in claim 9, wherein the axis of the light emitter is substantially parallel in relation to the axis of the light receiver.

12. The compliance monitor as claimed in claim 9, wherein the sensor further includes at least one lens adapted to refract the light emitted by the light emitter and/or the light to be received by the light receiver.

13. The compliance monitor as claimed in claim 9, wherein the light emitter is angled with respect to the light receiver.

14. The compliance monitor as claimed in claim 13, wherein the light emitter and the light receiver are angled toward each other.

15. The compliance monitor as claimed in claim 14, wherein the angle between the axis of the light emitter and the axis of the light receiver is between 40° to 120°.

16. The compliance monitor as claimed in claim 15, wherein the angle between the axis of the light emitter and the axis of the light receiver is approximately 60°.

17. The compliance monitor as claimed in claim 14, wherein the axis of the light emitter and the axis of the light receiver intersect at the surface of the medicament delivery device.

18. The compliance monitor as claimed in claim 8, wherein the beam of light transmitted by the light emitter and the beam of light received by the light receiver meet at the surface of the medicament delivery device.

19. The compliance monitor as claimed in claim 9, wherein the reflected light received by the light receiver is converted into a corresponding voltage.

20. The compliance monitor as claimed in claim 19, wherein the size of the voltage generated is indicative of the color or the wavelength signature of the medicament delivery device.

21. The compliance monitor as claimed in claim 19, wherein the ECM is further configured to calculate and/or determine the color of the wavelength signature of the medicament delivery device based on the nature of the reflected light and/or voltage generated.

22. The compliance monitor as claimed in claim 21, wherein the ECM further includes an algorithm to make the determination.

23. The compliance monitor as claimed in claim 1, wherein the sensor further includes a proximity sensor and/or a color sensor.

24. The compliance monitor as claimed in claim 2, wherein the ECM is further configured to detect the presence or absence of the medicament delivery device.

25. The compliance monitor as claimed in claim 23, wherein the proximity sensor determines that the compliance monitor is correctly attached to the medicament delivery device.

26. The compliance monitor as claimed in claim 1, wherein the medicament delivery device is a medicament inhaler that further includes:
a housing to contain the store of medicament, and
a mouthpiece for directing the dose of medicament into the mouth of a user.

27. The compliance monitor as claimed in claim 1, wherein the compliance monitor further includes a wireless communicator, for the wireless transmission of usage data to a computing device external to the compliance monitor or medicament delivery device.

28. A method for identifying a type of medicament delivery device associated with a compliance monitor, the method comprising:
identifying properties of the medicament delivery device to indicate the type of medicament delivery device using a recognition module associated with the compliance monitor, the recognition module including an infrared light sensor;
comparing the identified properties of the medicament delivery device with the known properties of the prescribed medicament delivery device, and
determining if the prescribed medicament delivery device is connected to the compliance monitor, wherein the identified properties of the medicament delivery device include a type of plastic material, the type of plastic material being indicative of the type of medicament delivery device.

29. The method as claimed in claim 28, further including notifying the user of the result of the determination via a user interface associated with the compliance monitor and/or transmission of the result of the determination to a computing device external to the compliance monitor or the medicament delivery device.

30. The method as claimed in claim 28, further including: wirelessly transmitting the result of the determination to a computing device external to the compliance monitor or medicament delivery device.

31. An optical sensor when used with a compliance monitor for monitoring usage and type of a medicament delivery device, the compliance monitor including a compliance monitor housing configured to attach to the medicament delivery device and a dose detector for determining when a dose of medicament is dispensed, and a recognition module including the optical sensor, the optical sensor comprising:
an IR light emitter and an IR light receiver, an axis of the light emitter being substantially parallel to an axis of light receiver;
a first portion including a base, which houses the IR light emitter, the IR light receiver and an IR divider which separates the IR light emitter from the IR light receiver;
a second portion including a molded cover which fits over the first portion;
the first and second portions being arranged and constructed such that a portion of the cover of the second portion that fits above the IR emitter or IR receiver is molded as a lens, and wherein:
each lens has a shape of a triangular prism, the vertical axis of which is rotated 90° away from the IR divider, and the base of which is cut off on an angle to allow the base to abut to the side of the IR divider;

the lens positioned over the light emitter is configured to refract the beam of emitted light by approximately 10° to 40°; and the lens positioned over the light receiver is configured to refract the reflected light beam by approximately 10° to 40, wherein the recognition module including the optical sensor is configured to identify a type of plastic material, the type of plastic material being indicative of the type of the medicament delivery device.

32. The optical sensor as claimed in claim 31, wherein the optical sensor is configured to detect objects at distances from 0.1 mm to 5 mm.

33. The optical sensor as claimed in claim 31, wherein the optical sensor is fitted into a compliance monitor.

\* \* \* \* \*